US006082118A

United States Patent [19]

Endrizzi et al.

[11] Patent Number: 6,082,118

[45] Date of Patent: Jul. 4, 2000

[54] STORAGE AND TRANSPORT OF GAS HYDRATES AS A SLURRY SUSPENION UNDER METASTABLE CONDITIONS

[75] Inventors: Fred P. Endrizzi, Fairfax, Va.; Robert F. Heinemann, Plano, Tex.; David Da-Teh Huang, Plano, Tex.; Jinping Long, Plano, Tex.; Roland B. Saeger, Runnemede, N.J.; Anthony A. Urbanelli, Herndon, Va.

[73] Assignee: Mobil Oil Corporation, Fairfax, Va.

[21] Appl. No.: 09/111,212

[22] Filed: Jul. 7, 1998

[51] Int. Cl.[7] ............................ F17C 11/00; C07C 9/00

[52] U.S. Cl. ............................ 62/46.1; 62/46.2; 585/15

[58] Field of Search ............................ 62/46.1, 46.2; 585/15

[56] References Cited

U.S. PATENT DOCUMENTS

| | | | |
|---|---|---|---|
| 2,270,016 | 1/1942 | Benesh | 48/190 |
| 2,375,559 | 5/1945 | Hutchinson et al. | 48/190 |
| 2,904,511 | 9/1959 | Donath | 210/59 |
| 3,170,870 | 2/1965 | Bachman | 210/59 |
| 3,514,274 | 5/1970 | Cahn et al. | 48/190 |
| 3,856,492 | 12/1974 | Klass . | |
| 3,888,434 | 6/1975 | Chersky et al. | 243/38 |
| 3,954,921 | 5/1976 | Yoshida et al. | 261/116 |
| 3,975,167 | 8/1976 | Nierman | 48/190 |
| 4,915,176 | 4/1990 | Sugier et al. | 166/371 |
| 4,920,752 | 5/1990 | Ehrsam | 62/46.1 |
| 4,930,319 | 6/1990 | Bee et al. | 62/69 |
| 5,473,904 | 12/1995 | Guo et al. | 62/46.1 |
| 5,536,893 | 7/1996 | Gudmundsson | 585/15 |
| 5,562,891 | 10/1996 | Spencer et al. | 423/437 |

FOREIGN PATENT DOCUMENTS

WO 93/01153 1/1993 WIPO .

OTHER PUBLICATIONS

1936 Index to Refiner and Natural Gasoline Manufacturer, A Gulf Publishing Company Publication, "The Solvent Dewaxing Process", by W. P. Gee, et al.., vol. 15 from Jan. to Dec. 1936 (pp. 205–209).

American Gas Association Monthly, Feb. 1946, vol. 28, No. 2, Hydrate Storage Natural Gas, by Benjamin Miller, et al., (pp. 63–67, p. 92).

Handbook of Natural Gas Engineering, Chapter 5, "Water–Hydrocarbon Systems", by Donald L. Katz (pp. 189–221).

Chemical Engineering Science, vol. 42, No. 7, 1987 "Kinetics of Methane Hydrate Decomposition", by H. C. Kim, et al., (pp. 1645–1653).

Soviet Geology and Geophysics, "The Dynamics of the Zone of Hydrate Formation and its Effect on the Temperature Regime of the Cryolithozone", by A. A. Trofimuk, et al., vol. 27, No. 11, 1986 (pp. 1–7).

(List continued on next page.)

*Primary Examiner*—William Doerrler

*Attorney, Agent, or Firm*—Robert B. Furr, Jr.; Malcolm D. Keen

[57] ABSTRACT

A suitable slurry composition allows gas hydrates to be stored or transported under metastable conditions. The slurry includes gas hydrate particles and a carrier liquid for the gas hydrate particles. Suitable carrier liquids have a specific gravity in the range from about 0.6 to about 2, a pour point below about −20° C. a viscosity of about 10 centipoise or less, and a thermal conductivity lower than that of the gas hydrate particles. The slurry can be stored or transported in a system that includes a container for holding the slurry; a device for agitating the slurry while in the container (e.g., a mixing blade, a rotating screw, a reciprocating box beam, or an ultrasound generator); a device for removing excess carrier liquid from the container while it is loaded or being loaded with gas hydrates and/or carrier liquid (e.g., a skimming device or a drain); and a device for reslurrifying the gas hydrates with carrier liquid before or during unloading of the gas hydrates from the container (e.g., a carrier liquid injection nozzle).

22 Claims, 2 Drawing Sheets

OTHER PUBLICATIONS

Newscientist, "Gas Hydrates Keep Energy On Ice", by Ian Ridley et al., Feb. 25, 1988 (pp. 53–58).

Industrial & Engineering Chemistry Research, A Publication of the American Chemical Society, "A Calorimetric Study of Naturally Occurring Gas Hydrates", by Y. Paul Handa, May 1988, vol. 27, No. 5. (pp. 872–874).

Theoretical Foundations of Chemical Engineering, Translated from Russian, "New Technologies Using Gas Hydrates", by L. F. Smirnov, vol. 23, No. 6, Nov.–Dec. 1989 (pp. 514–526).

Inzbenernaya Geologiya, "Experimental Investigations of the Microstructure of Agglomerate of Ice and Methane Hydrate", by E. D. Ershov, et al.. No. 3, (pp. 32–37) 1990.

The State–of–the–Art of Hydrates as Related to the Natural Gas Industry Final Report (Jan. 1990–Oct. 1991) Part 4. of a Project Entitled "The Economic Impact of Fluid Properties Data on the Gas Industry" by E. Dendy Sloan, Jr. for Gas Research Institute Contract No. 5086–260–1212, Jun. 1, 1992 (pp. 1–34).

Cold regions Science and Technology, 20 (1992), Elsevier Science Publishers B. V., Amsterdam, "Experimental Research on Gas Hydrate Decomposition in Frozen Rocks", by E. D. Ershov, et al.. (pp. 147–156).

Industrial & Engineering Chemistry Research, A publication of the American Chemical Society, Jul. 1993, 32 "Clathrate Hydrates", by Peter Englezos (pp. 1251–1274).

SPE Production & Facilities, "Storing Natural Gas as Frozen Hydrate", by J. S. Gudmundsson, et al., Feb. 1994, vol. 9, No. 1 (pp. 69–73).

Annals of the New York Academy of Sciences, vol. 715, "Overview—Gas Hydrate Geology and Geography" by Rodney D. Malone (pp. 225–231) (1994).

Annals of the New York Academy of Sciences, vol. 715, "Natural Gas Hydrate Occurrence and Issues", by Keith A. Kvenvolden (pp. 232–246) (1994).

The Proceedings of the Fifth (1995) International Offshore and Polar Engineering Conference, vol. 1, 1995 "*Transport of Natural Gas as Frozen Hydrate*", by J. S. Gudmundsson, et al. (pp. 282–288).

Advanced Technology, Leonard LeBlanc, Houston, "Natural Gas Transport as Hydrates 25% Below Cost of LNG".

Thesis "Gas Hydrate Formation Mechanism and Kinetic Inhibition" by Jinping Long, T–4265 (pp. 1–390).

McGraw–Hill Book Company, Third Edition, by Max S. Peters, et al., "Plant Design and Economics for Chemical Engineers" (pp. 575–586) (1980).

STORAGE AND TRANSPORT OF GAS HYDRATES AS A SLURRY SUSPENION UNDER METASTABLE CONDITIONS

FIELD OF THE INVENTION

This invention relates to a slurry composition that allows gas hydrates to be stored or transported under metastable conditions, a system for storing and transporting gas hydrates, and methods for storing and transporting gas hydrates. The slurry composition includes gas hydrate particles and a carrier liquid for the gas hydrate particles. After storage and/or transport, the gas hydrates can be regassified and the gas used for any suitable purpose.

BACKGROUND OF THE INVENTION

Gas hydrates have been known for many years. These hydrates are inclusion compounds wherein various light hydrocarbon gases or other gases, such as natural gas, associated natural gas, methane, ethane, propane, butane, carbon dioxide, hydrogen sulfide, nitrogen, and combinations thereof, physically react with water at elevated pressures and low temperatures. The gas becomes included or entrapped within the extended solid water lattice network which includes hydrogen bonded water molecules. The hydrate structure is stable due to weak van der Waals' forces between the gas and water molecules and hydrogen bonding between water molecules within the lattice structure.

An exemplary, non-stoichiometric reaction equation for the formation of natural gas hydrates is as follows:

$$CH_4(g)+mH_2O(l)\rightarrow CH_4(H_2O)m(s).$$

In this equation, the value "m" typically is 4 to 6, and the heat of formation ($\Delta H_f$) is −410 kJ/kg hydrate for methane hydrate, which is approximately 25% higher than the heat of fusion of water. The reverse reaction, exploited during regasification, is endothermic. Because gas hydrates are solids that form at a gas-water interface, the formation and regasification reactions are mass-transfer limited.

At least two different gas hydrate crystalline structures are known, each of which is a clathrate crystalline structure. A clathrate hydrate unit crystal of structure I includes two tetrakaidecahedron cavities and six dodecahedron cavities for every 46 water molecules. A clathrate hydrate unit crystal of structure II contains eight large hexakaidecahedron cavities and 16 dodecahedron cavities for every 136 water molecules. A relatively large volume of gas can be entrapped under pressure in these cavities. For example, it has been determined that natural gas hydrates can contain as much as 180 standard cubic feet of gas per cubic foot of the solid natural gas hydrates.

Early on, gas hydrates were considered an industrial nuisance. Petroleum and natural gas production facilities often are located in cold environments, where the product is located in deep underground or underwater wells. When tapping these wells, all of the necessary conditions and ingredients are present for producing gas hydrates—i.e., light hydrocarbon gases and water are present, the temperature is low, and the pressure is high. Therefore, gas hydrates often were produced spontaneously in the drilling and transmission pipes and equipment when an oil or natural gas well was tapped. Because gas hydrates are solid materials that do not readily flow in concentrated slurries or in solid form, when spontaneously produced in oil or natural gas production, they tend to clog the equipment, pipes, and channels in the production and transmission systems. These disadvantageous properties of gas hydrates spawned much research into methods for inhibiting hydrate formation and eliminating this nuisance. See, for example, D. Katz, et al., *Handbook of Natural Gas*, McGraw-Hill, New York (1959) pp. 189–221; and E. D. Sloan, Jr., *Clathrate Hydrates of Natural Gases*, Marcel Dekker, Inc. (1991). These documents are entirely incorporated herein by reference.

Because of the relatively high volume of gas that potentially can be stored in gas hydrates, however, eventually researchers began to look at this "nuisance" as a possible method for safely and cost effectively storing and/or transporting gases. See B. Miller, et al., *Am. Gas. Assoc. Mon.*, Vol. 28, No. 2 (1946), pg. 63. This document is entirely incorporated herein by reference. Several researchers and patentees have described methods and systems for producing gas hydrates. See, for example, U.S. Pat. No. 3,514,274 to Cahn, et al., which document is entirely incorporated herein by reference.

Gudmundsson describes various systems for producing gas hydrates. See, for example, U.S. Pat. No. 5,536,893; WO Patent Publication No. 93/01153; "Transport of Natural Gas as Frozen Hydrate," ISOPE Conference Proceedings, V1, The Hague, Netherlands, June 1995; and "Storing Natural Gas as Frozen Hydrate," SPE Production & Facilities, February 1994. These documents each are entirely incorporated herein by reference. In these documents, Gudmundsson discloses storing gas hydrates under "metastable" conditions, i.e., conditions under which one would normally expect the hydrates to be unstable and decompose. For example, in U.S. Pat. No. 5,536.893. Gudmundsson describes agglomerating gas hydrates into solid blocks suitable for long term storage at atmospheric pressure and at a temperature below 0 to −15° C. One would expect the hydrates to be unstable or decompose under these metastable conditions because these temperature and pressure conditions are not suitable for gas hydrate formation. Under relatively mild metastable conditions (e.g., 5 to 20° F. and ambient pressure), however, gas hydrates dissociate sufficiently slowly to remain intact for periods of time suitable to ocean transport or large-scale storage (e.g., for 10 days or more). This metastability phenomenon is attributed, at least in part, to spontaneous regasification of the outer surface of a macroscopic hydrate sample. Because the hydrate regasification process is endothermic, once the outer surface of the hydrate sample dissociates, auto-refrigeration freezes the dissociated water to create an ice shell that significantly insulates the bulk hydrates and attenuates the mass transfer rate of gas from within the interior of the sample.

Additionally, gas hydrates are effective insulators (thermal conductivity "k" of about 0.5 W/m K for hydrates, as compared to a thermal conductivity "k" of 2 for ice). This insulative property protects the interior gas hydrates in a bulk sample from heating and helps keep bulk gas hydrates from dissociating too rapidly. Thus, the metastability and insulative properties of gas hydrates allow them to remain stable under relatively mild conditions after they are initially produced.

Traditionally, hydrate-forming gases, such as natural gas, associated natural gas, methane, ethane, propane, butane, carbon dioxide, nitrogen, and hydrogen sulfide, have been stored under high pressures. Liquefied-natural gas ("LNG") and liquefied propane gas ("LPG") are examples of this type of storage system. Because of the need for high pressure cylinders, storage of gases under high pressures and liquefied conditions presents significant safety issues and is very expensive.

SUMMARY OF THE INVENTION

This invention relates to a slurry composition for storing and/or transporting gas hydrates, a system for storing and/or transporting gas hydrates, and various methods for storing and/or transporting gas hydrates. The invention takes advantage of the favorable properties of gas hydrates and the slurries and provides a safe convenient, and inexpensive system and method for storing and/or transporting gas hydrates.

In one aspect, this invention relates to a slurry composition for storing or transporting gas hydrates under metastable conditions. The slurry composition includes gas hydrate particles that hold at least one gas selected from the group consisting of natural gas, associated natural gas, methane, ethane, propane, butane, carbon dioxide, hydrogen sulfide, and nitrogen. The slurry composition further includes a carrier liquid for the gas hydrate particles. Suitable carrier liquids for use in this invention include those having a specific gravity in the range from about 0.6 to about 2, a pour point below about −20° C. a viscosity of about 10 centipoise or less, and a thermal conductivity lower than that of the gas hydrate particles.

Preferred carrier liquids for use in the invention have a thermal conductivity in the range from about 0.02 BTU/hr-ft-° F. to about 0.3 BTU/hr-ft-° F. Preferably, the thermal conductivity is less than that of the hydrate particles (e.g., less than about 0.289 BTU/hr-ft-° F.) and greater than that of insulation foams (e.g., greater than about 0.028 BTU/hr-ft-° F.). Additionally, it is preferred that the carrier liquid be non-toxic or have low toxicity (e.g., a lethal dosage ($LD_{50}$) in rats of about 10 mg/kg or higher). Suitable carrier liquids include pure hydrocarbon liquids; alcohols; glycols (both with and without water); kerosene; diesel oil; condensate oils; and lube oils.

Preferred gas hydrate particles for use in this invention have a density in the range from about 0.8 to about 1 g/$Cm^3$, with a density of about 0.9 g/$cm^3$ being particularly preferred.

Another aspect of this invention relates to a system for transporting or storing gas hydrates under metastable conditions. The system includes a container for holding a slurry of gas hydrate particles and a carrier liquid; a means for agitating the gas hydrate particles and carrier liquid while in the container; a means for removing excess carrier liquid from the container during or after loading of the container with gas hydrates and/or carrier liquid; and a means for adding carrier liquid to the container before or during unloading of the gas hydrates from the container. The means for adding and the means for agitating form a slurry of hydrate particles and carrier liquid which is then removed from the container. Preferably, for most economic use, all or most excess carrier liquid is removed from the container during loading so that a maximum amount of hydrate particles are stored and/or transported. Then, when the container is to be unloaded, carrier liquid is reinjected into the container to reslurrify the hydrate particles into a pumpable slurry to facilitate easy unloading.

Any suitable means for agitating the gas hydrate particles and carrier liquid can be used in this system without departing from the invention. For example, the agitation means can include a rotating mechanical screw; a reciprocating beam; a mixing blade; or an ultrasound generator. Any suitable number of these devices can be included in the system according to the invention, and these various types of agitating devices also can be used in combination.

Additionally, any suitable means for removing excess carrier liquid can be used in the system according to the invention. For example, a skimming device can be provided for removing carrier liquid located at a top surface of the slurry or container. If desired, this skimming device can be movable, depending on the desired level of the slurry. Alternatively, a drain can be provided for removing excess carrier liquid located at or near the bottom of the container.

As noted above, the system according to the invention includes a means for adding carrier liquid to the container before or during unloading of gas hydrates from the container. This means may include a device (e.g., a nozzle) for injecting carrier liquid into the container. Preferably, the carrier liquid is injected into the container at or near a location where a means for agitating the slurry mixes the gas hydrate particles and the carrier liquid.

Another system according to the invention includes a container, a means for removing excess carrier liquid, and a means for adding carrier liquid, as described above. This system, however, additionally includes a means for preventing or reducing adherence of ice or hydrate particles on an interior wall of the container. Preventing or reducing unwanted adherence to the container walls can be accomplished, for example, by making the interior surface of the container wall(s) very smooth. A smooth steel surface on the interior walls can be used for this purpose. Additionally or alternatively, the interior walls can be coated with anti-stick coatings (e.g., epoxy materials, paints, paraffinic alkanes, waxes, polytetrafluoroethylene (Teflon) or lubricating oils).

As another alternative, unwanted ice or hydrate adherence to the interior walls of the container can be prevented or reduced by inclining the interior wall or walls with respect to the vertical direction. Preferably, the wall or walls are inclined such that a cross-sectional area at an upper portion of the container is smaller than a cross-sectional area at a lower portion of the container. The incline angle of the walls is preferably in the range of from about 1° to about 10° from vertical.

The invention also relates to methods for storing or transporting gas hydrates. In a first method, a slurry of gas hydrate particles and a carrier liquid is formed, wherein the gas hydrate particles include at least one gas selected from the group consisting of natural gas, associated natural gas, methane, ethane, propane, butane, carbon dioxide, hydrogen sulfide, and nitrogen, and wherein the carrier liquid has a specific gravity in the range from about 0.6 to about 2, a pour point below about −20° C., a viscosity of about 10 centipoise or less, and a thermal conductivity lower than that of the gas hydrate particles. Slurries of this form can be used to store and/or transport gas hydrates under metastable conditions. Other suitable characteristics of the gas hydrates and the carrier liquid are described above.

Another method according to this invention includes adding a slurry of gas hydrate particles and a carrier liquid to a container; removing excess carrier liquid from the container during or after loading of the container with gas hydrates or carrier liquid; and reslurrifying the gas hydrate particles with carrier liquid before or during unloading of the gas hydrate particles from the container. This reslurrifying step can include agitating the gas hydrate particles and carrier liquid to form a pumpable slurry. Any suitable methods for removing excess carrier liquid from the container and reslurrifying the gas hydrates can be used in this aspect of the invention. For example, the skimming devices, drain devices, carrier liquid injectors, and agitators described above can be used.

BRIEF DESCRIPTION OF THE DRAWINGS

The advantageous aspects of the invention will be more fully understood and appreciated when considered in conjunction with the following detailed description and the attached figures, wherein.

DETAILED DESCRIPTION OF THE INVENTION

This invention relates to novel compositions, methods, and systems for storing and/or transporting gas hydrates, such as natural gas hydrates, under metastable conditions. Gas hydrate particles provided in a slurry composition according to the invention can be sustained without substantial melting or sedimentation for long periods of time (e.g., several weeks or months), thereby providing compositions suitable for long term storage or long distance transport. Thus, the compositions, systems, and methods according to the invention can be used for large-scale gas hydrate transport and/or storage. In use, the technology described herein can be linked with gas hydrate production at reserve sites and gas hydrate regasification locations to form a complete gas utilization chain that can reduce or obviate reliance on existing LNG sources.

In this application, the term “metastable conditions” is used to refer to temperature and pressure conditions under which one would normally expect gas hydrates to decompose or dissociate. Such conditions are not suitable for initial gas hydrate production. Metastable conditions are well known in this art and are described, for example, in Gudmundsson’s U.S. Pat. No. 5,536,893 discussed above. An example of suitable metastable conditions for storing and/or transporting natural gas hydrates according to this invention includes a pressure of about atmospheric pressure and a temperature between about −5° C. and about −20° C.

The compositions, systems, and methods according to this invention take advantage of three main features of the inventive gas hydrate system. Long term stability for gas hydrate storage and transport can be accomplished by appropriate selection of slurry carrier liquids, agitation mechanisms, and slurry vessel characteristics. These features of the invention will be described in more detail below along with the description of one preferred embodiment of the invention shown in FIG. 1.

Figure 1:
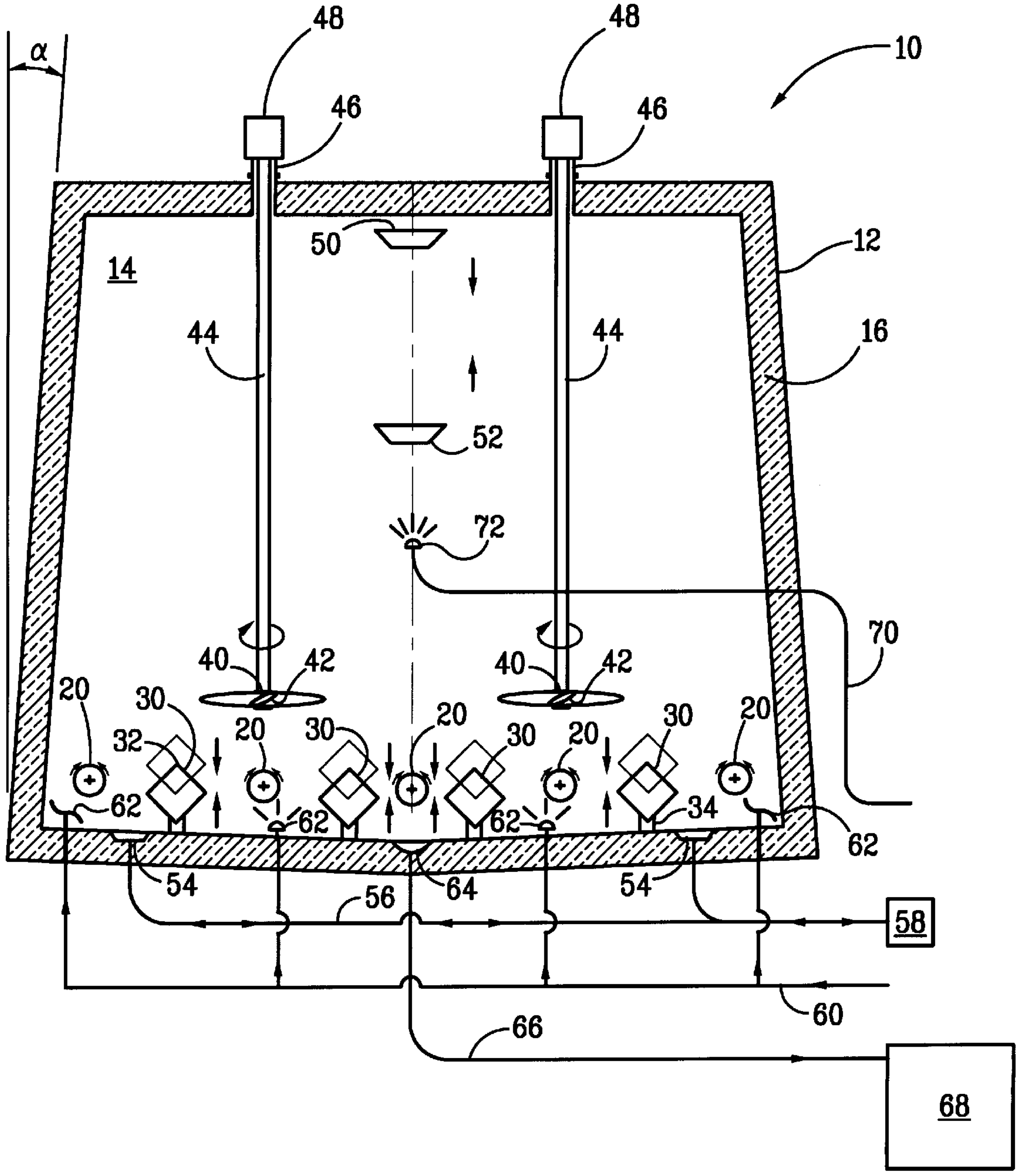
FIG. 1 shows a schematic cross-sectional view of a system for storing or transporting gas hydrates according to the invention.

A system 10 for storing and/or transporting gas hydrates is shown generally in FIG. 1. The system includes a vessel 12 with one or more insulated walls 16 that define a space 14 in which gas hydrate particles are held. As shown in FIG. 1, the vessel walls 16 can include stiffeners to maintain structural integrity. The vessel 12 can take on any suitable shape or form. For example, the vessel 12 can be cylindrical, spherical, rectangular, cubic, or any other appropriate shape. Additionally, the vessel 12 can constitute a hold of a ship, a tanker car, or other movable storage device. Preferred features of the vessel 12 design are described in more detail below.

According to the invention, gas hydrates are introduced into the vessel space 14 for storage and/or transport. It is well known that under relatively mild conditions (as compared to the conditions necessary to produce gas hydrates), gas hydrates will exist in a metastable condition and will dissociate sufficiently slowly to allow adequate time for long term storage, above-ground transport, or ocean transport. For example, natural gas hydrates will remain stable for more than 10 days under atmospheric pressure and at a temperature between about −5° C. and about −20° C. Under these conditions, natural gas hydrate particles have a density of about 0.9 $g/cm^3$.

A hydrate, on its own, can be difficult to handle efficiently because it is not a very pumpable material. As mentioned above, gas hydrates were originally considered a nuisance because they tended to clog gas production and transmission equipment. To maintain gas hydrate particles in a metastable state for storage and transport, and to facilitate handling of the particles (e.g., moving, pumping, etc.), the gas hydrates are introduced into the space 14 in the form of a slurry containing the gas hydrate particles and a carrier liquid. An appropriate carrier liquid for the gas hydrates must be selected to function as a suspension medium for the hydrate particles and to maintain stability of the hydrates for long term storage or transport. The carrier liquid also should provide a desired hydrate buoyancy under agitation during vessel transportation and during conditions where the slurry must flow (e.g., during loading and unloading of the vessel 12). An appropriate carrier liquid for use in this invention will not, under conditions of use, solidify within itself or crystallize with the hydrate particles.

The following physical properties provide guidelines for selection of an appropriate hydrate carrier liquid:

(a) a specific gravity between 0.6 and 2.0;

(b) a pour point below −20° C.;

(c) a viscosity less than 10 centipoise under the storage and pumping conditions;

(d) a low toxicity (lethal dosage in rats ($LD_{50}$) greater than about 10 mg/kg; and (e) a thermal conductivity in the range from about 0.02 BTU/hr-ft-° F. to about 0.3 BTU/hr-ft-° F. Preferably, the thermal conductivity is less than that of hydrate particles (e.g., less than about 0.289 BTU/hr-ft-° F.) and greater than that of insulation foams (e.g., greater than about 0.028 BTU/hr-ft-° F.).

Examples of suitable carrier liquids for use in the invention include pure hydrocarbon liquids having from 5 to 16 carbon atoms; lower alcohols (e.g., having 4 or fewer carbons, such as methanol and ethanol); glycols (both with and without water) (e.g., ethylene glycol); kerosene; diesel oil; condensate oils (e.g., those having 5 to 20 carbons); and lube oils. Liquefied natural gas, liquefied propane gas, and fresh water cannot be used as suitable hydrate slurry carrier liquids.

The various physical properties described above can be determined by any suitable, conventional method known to those skilled in the art. For example, the pour point (i.e., the temperature at which the liquid ceases to flow at atmospheric pressure) has been routinely used in describing the properties of kerosene and jet fuel. It can be measured by several methods, for example, using a standard test tube, a viscometer, a filter, and a small diameter flow loop. Similarly, the carrier liquid viscosity can be measured by any appropriate manner known in the art, such as using a Brookfield viscometer, a capillary viscometer, or simple pumping experiments.

The slurry is introduced into the vessel 12 from an appropriate source or mixer via inlet line 70 and nozzle 72. This inlet line 70 and nozzle 72 can be located at any suitable position in the vessel 12, and of course, more than one inlet can be provided. Once in the vessel 12, the slurry can be agitated to reduce hydrate agglomeration and to assist in keeping the hydrate and carrier liquid mixed. Any suitable agitation means, such as mechanical mixers or ultrasonic devices, can be used without departing from the invention. The agitation means can be manually or automatically controlled.

Various suitable agitation means are illustrated in FIG. 1. For example, mechanical screws 20 can be placed inside the vessel 12. As another example, reciprocating box beams 30 can be used in the vessel 12 to mix the carrier liquid and hydrate particles. Mixer blades 40 also can extend into the vessel 12 and maintain the hydrate particles in suspension in the carrier liquid. The agitation devices can be provided at any desired location within the vessel 12, and preferably in multiple locations, although, as shown in FIG. 1, it is preferred to include at least one agitation device at or near the bottom of the vessel 12, to assist in reslurrification and discharge of the hydrates from the vessel 12. This aspect of the invention will be described in more detail later in this application.

While the illustrated embodiment of the invention includes all of these different types of agitation devices, those skilled in the art will understand that any one or more of these agitation devices can be used individually or in any combination, depending on the needs of the system. These various agitation devices will be described below in more detail.

The vessel interior 14 includes one or more open mechanical screws 20, which, when rotated, agitate the hydrate particles and carrier liquid to produce or maintain the slurry. The screws 20 can be similar to those used in conventional mechanical screw conveyors, but without the surrounding trough or cover. In this manner, the mechanical screws 20 are exposed directly to the hydrate particles and can keep them mixed with the carrier liquid. Any suitable screw diameter and length can be used without departing from the invention, and these specific dimensions can be determined by the skilled artisan, through routine experimentation, to match the load from the slurry mixture to the available power.

The screws 20 are connected to an appropriate driving mechanism (e.g., a hydraulic motor, an electric motor, etc.) via a mechanical drive shaft supported on bearings. The drive mechanism and the bearings can be located either inside or outside of the interior vessel space 14. If outside, the drive shaft extends through the vessel wall 16 via a shaft seal that is used to prevent or reduce slurry leakage from the vessel 12.

In one embodiment of the invention, the driving mechanism is a hydraulic motor mounted outside the vessel 12 where a drive shaft extends through a wall 16 of the vessel 12. Hydraulic oil can be supplied to the motor through headers (pipelines) running outside of the vessel 12 with an appropriate system of branch lines and valves. The headers and motors can be controlled locally or remotely. Additionally, the motors can run in either direction (clockwise or counter-clockwise) by appropriately opening and closing selected valves. The hydraulic motors can be run either at high torque with slow speed or at low torque with high speed.

When a hydraulic motor is used as the power source, a pressure-compensating hydraulic pump, located either locally or remotely with respect to the hydrate storage vessel 12, supplies fluid under pressure to the main headers. The hydraulic pump is mounted on a common tank with filters, relief valves, and other equipment normally associated with a hydraulic power unit. The hydraulic pump can be driven by an electric motor or by a mechanical connection to an internal combustion engine as the power source. Suitable hydraulic motor and pump arrangements are commonly known and commercially available.

When the screws 20 are rotated by an electric motor, the screw shaft is mechanically coupled to the electric motor which can be located either inside or outside the storage vessel 12. Any suitable electric motor can be used without departing from the invention, such as a DC motor with speed control, an AC motor with variable frequency drive, an AC synchronous motor with a belt drive, or an AC synchronous motor with a gear reducer. Such motors are commercially available and commonly known to those skilled in this art.

Another possible agitating device for use according to this invention is a reciprocating box beam arrangement 30. One or more structural beams 30 are located within the vessel 12 to agitate the carrier liquid and hydrate particles to form or maintain the slurry. Agitation is provided in the illustrated embodiment by translating the beams 30 using a vertical (or substantially vertical) reciprocating motion. To ease the load on the beam and thereby reduce the force necessary to move it, the beam 30 can be constructed with a polygonal cross-section (e.g., square), with a corner 32 of the polygon pointed in the direction of movement. This reduces the force required to move the beam 30 because the comer 32 slices through the hydrate particles and slurry in a plow-like manner.

The size, length, and shape of the beam(s) 30 can be selected to equate the load from the slurry to the power available for moving the beam 30. Additionally, structural guides (not shown) can be provided to control movement of the beams 30 in the desired path of travel.

Slurry agitation is accomplished by moving box beams 30 in a vertical reciprocating manner. This can be done in any suitable manner, for example, using hydraulic cylinders 34 mounted between the box beam 30 and the bottom wall of the vessel 12. Preferably, two or more hydraulic cylinders 34 are provided per box beam 30. The hydraulic cylinders 34, which are commercially available, have adequate seals for operation in the hydrate environment with piping connections leading outside the vessel 12 and connecting to main hydraulic headers via valves to control operation of the cylinders. This cylinder control can be provided locally or remotely, and it can be accomplished automatically or on an "as needed" basis, as determined by an operator. The hydraulic system used to operate these cylinders, like the hydraulic motor system for rotating the screws 20 described above, is conventional, commercially available, and well known to those skilled in the art.

Agitation also can be provided in the system according to the invention by one or more rotating blade agitators 40. Rotating blades 40 at a relatively slow speed (e.g., about 1 to 20 rpms) can maintain the hydrate particles in suspension in the carrier liquid, at least in the area surrounding the blades 40. Additionally, like the other agitation devices described above, the blades 40 also can be used for reslurrification during hydrate discharge. The blades 40 are mounted to a hub 42 on a shaft 44. Preferably the shafts 44 are vertical or substantially vertical, and the blades 40 are mounted so as to rotate on a horizontal or substantially horizontal plane. The orientation, diameter, and pitch of the blades 40 can be appropriately selected by the skilled artisan to equate the load from the mixture to the available power. As an example, the blades 40 may have a diameter in the range from about 2 to 4 meters.

The blade shaft 44 is supported by a bearing 46 that may be located either inside or outside the vessel 12. A shaft seal protects against hydrate or slurry leakage at the location where the shaft penetrates the vessel wall 16. The blades 40 are power driven by a drive mechanism 48, preferably located outside the vessel 12. This drive mechanism 48 can be the same as or similar to any of those described above for driving the screw mechanisms 20.

Additionally, as noted above, agitation can be provided by one or more ultrasound devices (not shown) that bombard the hydrate particles with ultrasonic waves to break up any agglomeration. Such ultrasonic devices are known in the art. For example, devices similar to those used for lithotomy that can concentrate sonic waves on specific areas can be used to agitate the hydrate particles and assist in mixing the hydrate particles with carrier liquid to form or maintain a slurry.

To improve the economics during transport and storage of the gas hydrate particles, it is preferred that excess carrier liquid be removed from the slurry after or while the slurry is loaded into the vessel 12. By removing the excess carrier liquid, the hydrate carrying capacity of the vessel is significantly increased and the amount of deadweight transported in the form of carrier liquid is reduced. Ideally, all excess carrier liquid will be removed so that the only carrier liquid remaining in the vessel 12 during storage and/or transport is that amount of liquid necessary to fill the voids between hydrate particles. In reality, during slurry storage and/or transport, the hydrate concentration in the carrier liquid will be 50% by volume or higher, and preferably in the range of 75% to 98% by volume, based on the total volume of the slurry. Removal of the excess carrier liquid can convert the slurry composition in the vessel 12 into a highly concentrated slurry that is not readily pumpable although it is not necessary in all cases to remove that much of the carrier liquid.

The above preferred situation can be accomplished using the storage/transport system 10 according to the invention. To effectively remove excess carrier liquid from the vessel 12, an appropriate means for removing the carrier liquid must be provided. The arrangement and components of a proper removal system depend on the relative specific gravity of the carrier liquid vis-a-vis that of the hydrate particles. When the specific gravity of the carrier liquid is less than that of the hydrate, excess carrier liquid can be removed by skimming it off the top surface of the slurry held in the vessel 12, because the hydrate particles will sink in the liquid. On the other hand, when the specific gravity of the carrier liquid is greater than that of the hydrate, excess carrier liquid can be drained from the bottom of the vessel 12, because the hydrate particles float in the liquid. In either system, measuring devices can be provided with the vessel 12 to advise operators of the slurry level in the vessel 12, the hydrate level in the vessel 12, and the consistency of the slurry within the vessel 12 (i.e., the amount of hydrate in the slurry). Two suitable carrier liquid removal systems will be described in more detail below.

When the specific gravity of the carrier liquid is less than the specific gravity of the hydrate particles, the hydrate particles will settle to the bottom of the vessel 12 and excess carrier liquid will be present above these hydrates. To skim excess carrier liquid from the vessel 12, a trough 50 is fixed at the top of the vessel 12, at the full level of the vessel 12. As the level of the carrier liquid raises over the level of the trough 50, excess liquid will flow over the edges and into the trough 50. From there, the liquid is moved outside of the vessel 12 through its associated piping, where it is collected and pumped back to storage or the loading or transfer site. The trough 50 can be constructed from any suitable material, such as plastic or steel.

As another alternative or option, a skimming trough 52 can be provided that is movable within the vessel 12. In this alternative carrier liquid can be removed from the vessel 12 before it is completely filled with hydrate particles and liquid. Movement of the trough 52 can be accomplished by any suitable mechanism, such as hydraulic cylinders, flexible rigging (e.g., wire, ropes, chains, etc.), or by power screws. To facilitate movement of the trough 52, retractable or flexible connections (e.g., hoses) are provided to connect the trough 52 outlets to the fixed piping for transporting the carrier liquid out of the vessel 12.

When the specific gravity of the carrier liquid is greater than that of the hydrate particles, the hydrate particles will float atop the carrier liquid. In this instance, the excess carrier liquid is more easily removed at the bottom of the vessel 12. Drain wells 54 are provided to drain excess carrier liquid from the vessel 12, where it can be moved via pipeline 56 to an appropriate location 58 for storage, recycle, loading, transfer etc. Draining off excess carrier liquid can begin as soon as there is sufficient slurry in the vessel 12 to cause separation of the mixture by gravity.

For most economic and efficient operation of the system, a maximum amount of carrier liquid is removed for transport or storage of the gas hydrate particles. In this way, the maximum amount of hydrate particles are transported, stored, and/or maintained under metastable conditions and a minimum amount of the carrier liquid is moved or stored. When the hydrates reach their final destination or are to be moved or regasified an independent carrier liquid source can be used for reslurrification during hydrate unloading.

As excess carrier liquid is either skimmed from the top of the vessel 12 or drained from its bottom, hydrate particles can be carried along with the liquid. This is undesirable because it constitutes a loss of the valuable hydrate product. To prevent this loss, screens are provided at the liquid outlets in the troughs 50 and/or 52 and/or drains 54 to prevent the hydrate particles from leaving the vessel 12 along with the carrier liquid. Depending on the relative specific gravities of the carrier liquid and hydrate particles, as well as the setting time, these screens can become plugged with hydrate particles. To prevent plugging and to ensure effective operation of the system, a backwash system can be provided, e.g., in line 56. This backwashing is provided by periodically reversing the flow of excess carrier liquid and pumping the liquid back through the screens and into the vessel 12, thereby clearing the screens of hydrates.

If desired, separate holding tanks can be provided to store the volume of carrier liquid necessary to perform this backwashing function. Flow sensors can be provided, for example, in the pipeline 56, to indicate when the flow of carrier liquid has decreased to the point where backwashing is required to restore the desired level of performance of the system. Using such a system, backwashing can be controlled automatically, although it is possible to manually control the backwashing system, if desired.

While it is preferred that the backwashing system introduce the same carrier liquid into the vessel 12, any other suitable and compatible backwashing liquid can be used without departing from the invention.

As described above, for most economic, efficient, and effective use of the system in accordance with the invention, a maximum amount of excess carrier liquid is removed from the hydrate particles during actual storage and/or transportation of the hydrate particles. Preferably, all excess carrier liquid is removed such that the slurry includes only enough carrier liquid to fill the void spaces between hydrate particles. When this occurs, the vessel 12 is filled with a slurry that is highly concentrated with hydrate particles.

Gas hydrate particles alone or in highly concentrated slurries, however, are difficult to handle because they are not readily pumpable. In the form in which they are transported in this preferred embodiment, the highly concentrated slurries in the vessel 12 typically can not be readily pumped out of the vessel 12. Therefore, the system 10 according to the invention also provides a means for adding carrier liquid to the vessel 12 to thereby "re-slurrify" the hydrates into a pumpable slurry when the time comes to unload the hydrates from the vessel 12. To easily unload the hydrates by a slurry pump, a proper volumetric ratio of hydrate to carrier liquid must be present in the mixture. For example, a slurry typically remains pumpable even when the gas hydrate concentration is above about 20% by volume, and preferably above 30% by volume (based on the total volume of the slurry). If the slurry remains pumpable, gas hydrate concentrations between 50% and 85% by volume can be used during pumping and slurry unloading. For efficiency, it is preferred to pump a slurry having as high a gas hydrate concentration as possible, to limit unnecessary or excess movement of carrier liquid. The optimum hydrate concentration for slurry storage and pumping, which depends, inter alia, on the mechanical and transport properties of the hydrate and carrier liquid, can be readily determined by the skilled artisan using routine experimentation.

The pumpable slurry is provided according to the invention using a means 60 for injecting carrier liquid into the vessel 12. This means 60 includes one or more carrier liquid injectors 62. These injectors 62 can be, for example, fixed or rotating nozzles that discharge carrier liquid into the stored hydrate particles, preferably in the vicinity of a slurry agitator. Although any suitable carrier liquid can be used for re-slurrifying, to assure compatibility and avoid unnecessary separation steps, preferably the same carrier liquid is used for reslurrifying as that used when the slurry was originally introduced into the vessel 12.

As the carrier liquid and hydrate particles are mixed by the agitators, a pumpable slurry is again formed. Drain wells 64 are provided at the bottom of the vessel 12 to collect the slurry mixture and pump it out, via pipeline 66, to a receiving tank 68 or other location for appropriate use or storage of the gas hydrates (e.g., re-gasification). If desired, a portion of the slurry can be reintroduced into the vessel 12 via inlet line 70 and nozzle 72. Reintroduction of the slurry helps the entire contents of the vessel 12 more rapidly re-slurrify and reach a pumpable state.

It may not be absolutely necessary to agitate the slurry during extended periods of storage or transport, particularly if the gas hydrates will be dissociated directly in the storage vessel 12. If the gas hydrates are to be discharged from the storage vessel 12, however, then agitation, at least periodically, during storage or transport will likely be necessary. Ideally, agitation will be limited as much as possible, and preferably, if practical, agitation can be limited to reslurrification and discharge. Alternatively, if desired, the slurry can be continuously agitated during transport or storage.

The mixture of hydrates and carrier liquid can be monitored by measuring devices to determine when the slurry mixture is of a suitable consistency for pumping and/or when all the hydrate has been discharged (i.e., when only carrier liquid is being pumped out). After the vessel 12 is emptied, it can be cleaned, stripped, and made ready for its next use.

When storing hydrate or discharging it from the vessel 12, it is desirable that the hydrate or any in situ formed ice not adhere to the vessel walls 16. It is anticipated that during use, some heat will transfer from outside of the insulated vessel walls 16 to the hydrate adjacent to the wall. causing some of the hydrate to dissociate to gas and water. Because the vessel temperature is maintained under conditions at which water will freeze (e.g., −10° C. and atmospheric pressure), this dissociated water may form ice that could adhere to the side walls 16 of the vessel 12. Additionally, hydrate particles in the vessel 12 can adhere to this formed ice and stick to the vessel walls 16. This build-up of stuck ice and hydrate particles is undesirable because it impedes slurry movement and results in a loss of gas product.

To reduce the likelihood of ice formation and adherence of ice and hydrates to the vessel walls 16, preferred embodiments of the vessel 12 include special features designed to reduce or eliminate this problem. First, the interior walls of the vessel 12 are made from very smooth steel plate (or other suitable material) with stiffeners and insulation on the outside thereof to maintain the structural shape of the vessel 12 and to reduce heat transfer through the vessel walls 16. Preferably, the steel for the structure will have a blast and prime coat prior to fabrication. When the vessel 12 is built, the interior surface of the walls 16 should have all burrs, scars, and weld slag removed, because such surface irregularities provide areas for water adherence and ice/hydrate build-up.

Additionally, the inside surfaces of the steel plates (i.e., the portions in contact with the hydrates) are preferably painted, e.g., with an epoxy or polyurethane paint. As an alternative, the interior wall surface can be lined with sheets of ultra high molecular weight polyethylene. To appropriately function to reduce ice or hydrate adherence, both the paint and the lined sheets should have low coefficients of friction, high abrasion resistance, zero moisture adsorption, and excellent corrosion resistance.

Anti-sticking chemicals can be applied to the interior vessel walls either in combination with the paint or in place of the paint. The type of anti-sticking chemicals needed will depend on the type of slurry carrier liquid used. For oil-based carrier liquids, such as condensate oils or kerosene, the liquid itself may provide enough lubricant effect to keep the hydrate particles from sticking to the vessel walls. For alcohol-based carrier liquid systems (e.g., methanol, glycol, etc.), anti-sticking chemicals should be insoluble in alcohol and should be applied to provide a smooth coverage on the interior vessel walls 16. Examples of suitable anti-sticking chemicals include long-chain paraffinic alkanes, waxes, and lubricating oils. If applied in combination with paint, the anti-sticking chemicals can either be pre-mixed with the aforementioned wall paints or applied after painting.

Another structural feature for reducing ice or hydrate particle accumulation on vessel walls 16 includes providing inclined vessel walls. As shown in FIG. 1, the vessel 12 has side walls 16 that incline inward from the bottom of the vessel 12 to its top. In this manner, the cross-sectional area of the vessel 12 is larger at the vessel bottom as compared to the cross-sectional area at its top. When so inclined, any ice formed against the wall will not be supported by friction as in a vertical wall, nor by gravity and friction as is the case with walls sloped outwardly from bottom to top. The degree of inward inclination (angle $\alpha$ in FIG. 1) should be high enough to provide natural gravitational fall of hydrate particles from the walls, but low enough to allow slurry homogeneity under agitation conditions. Typical wall inclinations, from the vertical direction, should be in the range between about 1° to about 10° on each side of the vessel 12.

The system according to the invention is well suited for use or construction as the cargo hold of a ship for transporting gas hydrates. One possible cargo hold design including multiple hydrate storage vessels 12 is illustrated in FIG. 2, which includes various dimensions, for a 40,000 deadweight ton slurry vessel based on the following particulars:

| | | |
|---|---|---|
| Ship length between perpendiculars ($L_{BP}$) | 185.0 | m |
| Ship beam (B) | 32.3 | m |
| Ship depth (D) | 18.6 | m |
| Draft, design (T) | 10.4 | m |
| Skimming trough width (top) ($W_{tr, top}$) | 3.6 | m |
| Skimming trough depth ($D_{tr}$) | 1.0 | m |
| Skimming trough width (bottom) ($W_{tr, bot}$) | 1.8 | m |
| Agitating blade diameter ($D_b$) | 2.5 | m |
| Screw agitator length ($L_{ag}$) | 12.3 | m |
| Length of one cargo tank ($L_c$) | 25.2 | m |
| Number of cargo tanks | 10 | |
| Service speed ($V_s$) | 15.0 | knots |
| Power (MCR) | 16,000 | BHP |
| Cargo, deadweight tons | 40,000 | dwt |
| Ship, deadweight tons | 41,080 | dwt |
| Total cargo tank volume | 45,600 | $m^3$ (@ 98% load) |

The deadweight and volume calculations above assumed a slurry composed of 81.7% solid hydrate particles and 18.3% of a kerosene carrier liquid. The insulation necessary for hydrate metastability, during a voyage of 500 nautical miles one way, included 2-layers of 4 inch thick polyurethane rigid foam (2 lb/$ft^3$), plus a glass reinforced plastic ("GRP") fiberglass vapor barrier. The total gas hydrate volume will melt less than 0.1% by weight during the trip. The vessel hold material is a grade 316 stainless steel with an average thickness of 7/16 inch.

Figure 2:
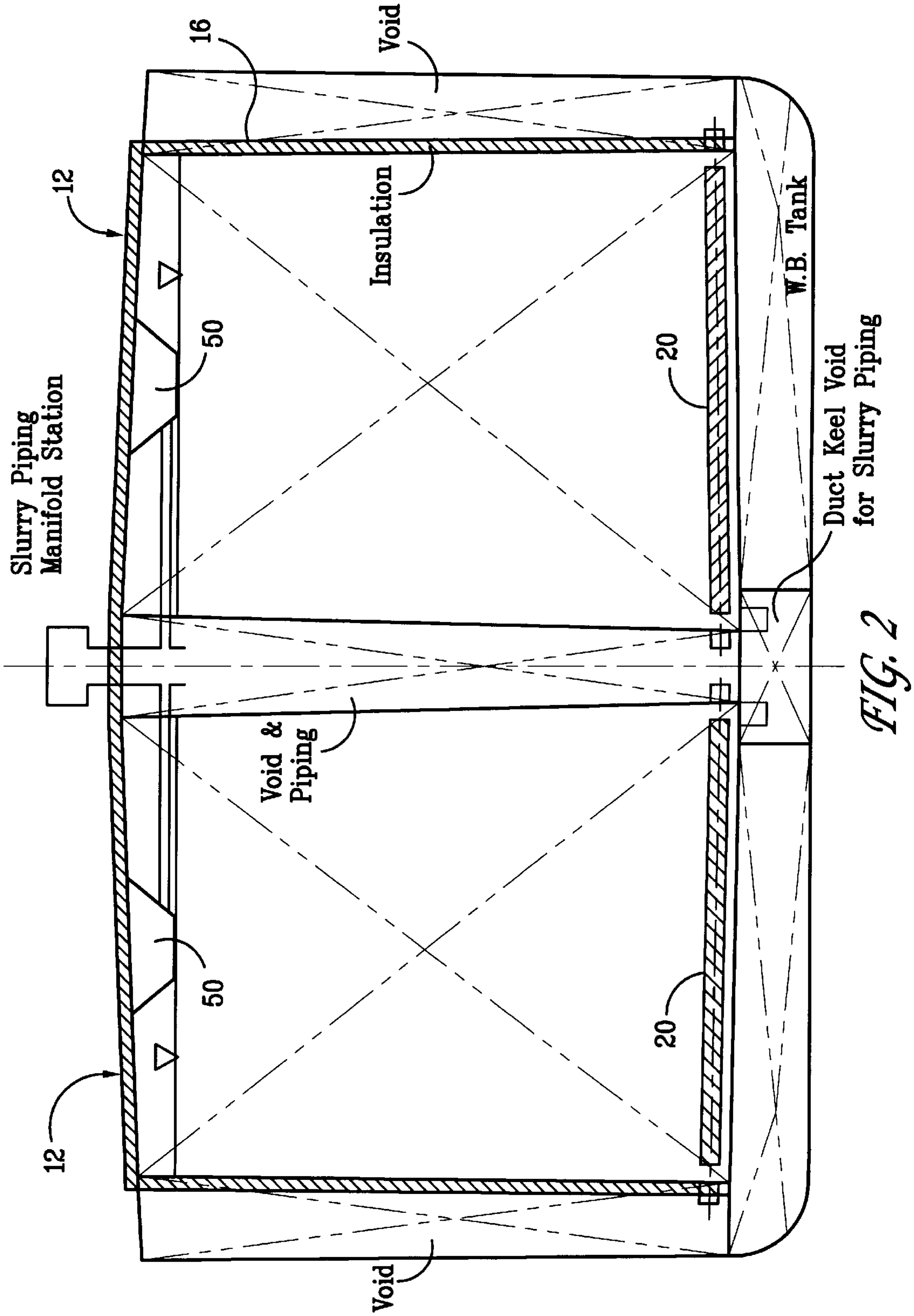
FIG. 2 shows a schematic cross-sectional view of the system according to the invention used as a cargo hold in a ship.

The embodiment of FIG. 2 is advantageous because more than one cargo tank 12 can use common piping, hydraulic fluid sources, carrier liquid sources, etc. As described above, 10 cargo tanks 12 are provided in this single ship.

In describing this invention Applicants have set forth certain theories and mechanisms in an effort to explain how and why the invention works in the manner in which it works. These theories and mechanisms are set forth for information purposes only. Applicants are not to be bound by any specific physical, chemical, or mechanical theories or mechanisms of operation.

While the invention has been described in terms of various preferred embodiments using specific examples, those skilled in the art will recognize that various changes and modifications can be made without departing from the spirit and scope of the invention, as defined in the appended claims.

We claim:

1. A slurry for storing or transporting a gas hydrate under metastable conditions, comprising:

gas hydrate particles including at least one gas selected from the group consisting of natural gas, associated natural gas, methane, ethane, propane, butane, carbon dioxide, hydrogen sulfide, and nitrogen; and a carrier liquid for the gas hydrate particles, wherein the carrier liquid has a specific gravity in the range from about 0.6 to about 2, a pour point below about −20° C., a viscosity of about 10 centipoise or less, and a thermal conductivity lower than that of the gas hydrate particles.

2. A slurry according to claim 1, wherein the thermal conductivity of the carrier liquid is in the range from about 0.02 BTU/hr-ft-° F. to about 0.3 BTU/hr-ft-° F.

3. A slurry according to claim 1, wherein the carrier liquid includes at least one material selected from the group consisting of an alcohol, a glycol, a kerosene, a condensate oil, and a lube oil.

4. A system for transporting or storing a gas hydrate, comprising:

a container for holding a slurry including gas hydrate particles and a carrier liquid, wherein the container maintains the gas hydrate particles under metastable conditions;

means for agitating the gas hydrate particles and carrier liquid while in the container;

means for removing excess carrier liquid from the container during or after loading of the container with gas hydrates or carrier liquid; and means for adding carrier liquid to the container before or during unloading of the gas hydrates from the container, wherein the means for adding and the means for agitating produce a slurry of gas hydrate particles and carrier liquid which is removed from the container.

5. A system according to claim 4, wherein the means for agitating includes at least one of the following: a mechanical screw; a movable beam; a mixing blade; or an ultrasound generator.

6. A system according to claim 4, wherein the means for removing excess carrier liquid includes a skimming device for removing carrier liquid located at or above a top surface of the slurry.

7. A system according to claim 6, wherein the skimming device is movably mounted in the container.

8. A system according to claim 4, wherein the means for removing excess carrier liquid includes a drain for removing carrier liquid located at or proximate a bottom surface of the container.

9. A system for transporting or storing a gas hydrate, comprising:

a container for holding a slurry containing gas hydrate particles and a carrier liquid, wherein the container maintains the gas hydrate particles under metastable conditions;

means for preventing or reducing adherence of ice particles or hydrate particles on an interior wall of the container;

means for removing excess carrier liquid from the container during or after loading of the container with gas hydrates or carrier liquid; and means for adding carrier liquid to the container before or during unloading of the gas hydrates from the container, wherein the means for adding and the means for agitating produce a slurry of gas hydrate particles and carrier liquid which is removed from the container.

10. A system according to claim 9, wherein the means for preventing or reducing adherence includes at least one smooth interior wall in the container.

11. A system according to claim 10, wherein the smooth interior wall is coated with an anti-stick coating.

12. A system according to claim 11, wherein the anti-stick coating includes a material selected from the group consisting of: a paint, a paraffinic alkane, a wax, polytetrafluoroethylene, and a lubricating oil.

13. A system according to claim 9, wherein the means for preventing or reducing adherence includes at least one inclined interior wall with respect to a vertical direction, wherein the wall or walls are inclined such that a cross-sectional area at an upper portion of the container is smaller than a cross-sectional area at a lower portion of the container.

14. A system according to claim 13, wherein at least one interior wall is inclined at an angle between about 1° and about 10° from vertical.

15. A method for storing or transporting a gas hydrate, comprising:

forming a slurry of gas hydrate particles and a carrier liquid, wherein the gas hydrate particles include at least one gas selected from the group consisting of natural gas, associated natural gas, methane, ethane, propane, butane, carbon dioxide, hydrogen sulfide, and nitrogen, and wherein the carrier liquid has a specific gravity in the range from about 0.6 to about 2, a pour point below about −20° C., a viscosity of about 10 centipoise or less, and a thermal conductivity lower than that of the gas hydrate particles; and holding the slurry under metastable conditions for the gas hydrate during storage or transport.

16. A method according to claim 15, wherein the carrier liquid includes at least one material selected from the group consisting of an alcohol, a glycol, a kerosene, a condensate oil, and a lube oil.

17. A method according to claim 15, wherein the metastable conditions include maintaining the slurry at about atmospheric pressure and at a temperature in the range from about −5° to about −20° C.

18. A method for transporting or storing a gas hydrate, comprising:

placing a slurry containing gas hydrate particles and a carrier liquid in a container;

removing excess carrier liquid from the container during or after loading of the container with gas hydrate particles or carrier liquid; and reslurrifying the gas hydrate particles with a carrier liquid before or during unloading of the gas hydrate particles from the container.

19. A method according to claim 18, wherein the reslurrifying includes agitating the gas hydrate particles and carrier liquid to form a pumpable slurry.

20. A method according to claim 18, wherein the removing includes skimming carrier liquid from a top surface of the liquid.

21. A method according to claim 18, wherein the removing includes draining carrier liquid from the container.

22. A method according to claim 18 wherein the reslurrifying includes injecting carrier liquid into the container.

* * * * *